United States Patent [19]

Wakabayashi et al.

[11] Patent Number: 4,656,172
[45] Date of Patent: Apr. 7, 1987

[54] 1-[5-(3,4,5-TRIMETHOXY PHENYL)-2,4-PENTADIENOYL]-4-(SUBSTITUTED CARBONYLMETHYL)-PIPERAZINES HAVING VASODILATING ACTIVITY

[75] Inventors: Toshio Wakabayashi, Tama; Takahiro Kumonaka, Kawasaki; Yasushi Suwabe, Tokyo, all of Japan

[73] Assignee: Terumo Kabushiki Kaisha, Tokyo, Japan

[21] Appl. No.: 776,625

[22] Filed: Sep. 16, 1985

[30] Foreign Application Priority Data

Sep. 17, 1984 [JP] Japan .................. 59-194253

[51] Int. Cl.$^4$ .................. A61K 31/505; C07D 403/00
[52] U.S. Cl. .................. 514/252; 544/372; 544/391
[58] Field of Search .................. 514/252; 544/372, 391

[56] References Cited

U.S. PATENT DOCUMENTS

| 3,407,199 | 10/1968 | Pachter | 544/372 |
| 3,410,857 | 11/1968 | Schoen et al. | 544/391 |
| 3,634,411 | 1/1972 | Faurau et al. | 544/391 |
| 4,029,650 | 6/1977 | Raymond et al. | 544/391 |

FOREIGN PATENT DOCUMENTS

| 58316 | 3/1969 | France | |
| 2516510 | 5/1983 | France | 544/391 |
| 2520618 | 8/1983 | France | 544/372 |
| 8172380 | 10/1983 | Japan | 544/391 |
| 8194873 | 11/1983 | Japan | 544/391 |
| 8189170 | 11/1983 | Japan | 544/391 |

OTHER PUBLICATIONS

Chemical Abstracts, vol. 88, No. 19, May 8, 1978, p. 503, No. 136267s, B. Vig et al., "Synthesis of Analogs of G-Phenylpenta-Trans-2, Trans-4-Dienoic Acid Amide" & Indian J. Chem., Sect. B 1977, 15B(11), 1048-1049.

Primary Examiner—Donald G. Daus
Assistant Examiner—Cecilia Shen
Attorney, Agent, or Firm—Burns, Doane, Swecker & Mathis

[57] ABSTRACT

There are disclosed novel piperazine derivatives and vasodilators containing the same. The compounds are useful for controlling or preventing vascular disorders such as cerebral embolism, myocardial infarction and limb arterial obstruction. As typical compounds are mentioned 1-[5-(3,4,5-trimethoxyphenyl)-2,4-pentadienoyl]-4-(pyrrolidinocarbonylmethyl)-piperazine, 1-[5-(3,4,5-trimethoxyphenyl)-2,4-pentadienoyl]-4-(N-isopropylaminocarbonylmethyl)-piperazine, 1-[5-(3,4,5-trimethoxyphenyl)-2,4-pentadienoyl]-4-(N,N-dimethylaminocarbonylmethyl)piperazine and 1-[5-(3,4,5-trimethoxyphenyl)-2,4-pentadienoyl]-4-(methylaminocarbonylmethyl)-piperazine.

7 Claims, No Drawings

1-[5-(3,4,5-TRIMETHOXY PHENYL)-2,4-PENTADIENOYL]-4-(SUBSTITUTED CARBONYLMETHYL)-PIPERAZINES HAVING VASODILATING ACTIVITY

BACKGROUND OF THE INVENTION

1. Field of the Invention

This invention relates to piperazine derivatives, vasodilators containing the same and a vasodilating method for vascular disorders. The piperazine derivatives provided by the present invention are novel compounds which have potent vasodilating activities. Therefore, they are useful for the therapy of vascular disorders such as cerebral, coronary and peripheral vascular diseases, which are to be treated by increasing blood flow.

2. Description of the Prior Art

Vascular diseases occuring after cerebral embolism, myocardial infarction or the like have recently taken a large portion of adult diseases, and development of drugs effectively preventing such disorders is highly desirable.

There have been developed a large number of vasodilators including derivatives of 3,4,5-trimethoxycinnamic acid such as, for example, 1-[3-(3,4,5-trimethoxyphenyl)-2-propenoyl]-piperazine (cinepazide), which are not necessarily satisfactory in efficacy of the drug.

SUMMARY OF THE INVENTION

As a result of our extensive studies on the pharmacological activities of a variety of piperazine derivatives which were synthesized starting with 5-(3,4,5-trimethoxyphenyl)-2,4-pentadienoic acid, we have found that the compounds of the invention have excellent vasodilating activities. The present invention is based upon the above finding.

Therefore, it is an object of the invention to provide novel piperazine derivatives and vasodilators containing the same as well as to provide a vasodilating method for vascular disorders.

DETAILED DESCRIPTION OF THE INVENTION

According to the present invention, there are provided piperazine derivatives represented by the general formula

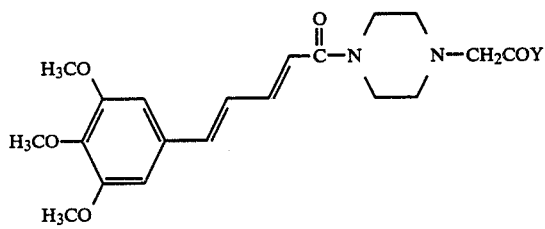

(I)

wherein Y represents pyrrolidyl group or a lower alkylamino group.

Further, according to the invention, a vasodilator containing a medically effective amount of the piperazine derivative represented by the above-mentioned general formula (I) and a method for controlling or preventing vascular disorders are provided.

Further, a pharmaceutical composition for the treatment of vascular disorders comprising a vasodilating amount of a piperazine derivative having the formula (I) together with a pharmaceutically acceptable carrier or diluent.

As the preferable amino group in the above formula (I) are mentioned methylamino, ethylamino, isopropylamino, propylamino, butylamino, dimethylamino or diethylamino.

Vasodilators as used herein means pharmaceutical preparations that have vasodilating activities to increase blood flow.

The piperazine derivatives of the above formula (I) are obtained by reacting thiazolidinethionamide of 5-(3,4,5-trimethoxyphenyl)-2,4-pentadienoic acid with piperazine to give 1-[5-(3,4,5-trimethoxyphenyl)-2,4-pentadienoyl]-piperazine which is then condensed with a chloroacetic amide of the formula $ClCH_2\,COY$ wherein Y has the same meaning as defined above.

The piperazine derivatives of the invention represented by the above-mentioned formula (I) can also be converted to acid addition salts. The acid addition salts thus obtained are within the scope of the invention. As the acid salts are preferably mentioned the salts with a mineral acid such as hydrochloric acid or sulfuric acid and the salts with an organic acid such as acetic acid, maleic acid, fumaric acid or malic acid.

The piperazine derivatives of the invention can be used as vasodilators effectively acting on cerebral, coronary and peripheral vascular and other diseases, the dosage of which is generally from 50 to 1500 mg per day, divided, as needed, into 1 to 3 doses. The route of administration is desirably by oral administration, but possibly by intravenous injection.

The piperazine derivatives of the invention are incorporated with pharmaceutical carriers or excipients by conventional methods to formulate tablets, powders, capsules or granules. As examples of the carrier or excipient are mentioned calcium carbonate, calcium phosphate, starch, sucrose, lactose, talc, magnesium stearate and the like. The piperazine derivatives of the invention can also be formulated in liquid preparations such as oily suspension, syrup or injectable solution.

This invention will be described in more details by means of examples and results of general pharmacological tests for determining the vasodilating activity as well as of acute toxicity tests.

EXAMPLE 1

To a solution of 1090 mg (12.65 mmol) of piperazine in a mixed solvent of 8 ml of water and 8 ml of tetrahydrofuran was added a solution of 500 mg of 5-(3,4,5-trimethoxyphenyl)-2,4-pentadienoic thiazolidinethionamide in 3 ml of tetrahydrofuran. The mixture was reacted at room temperature for 1 hour. To the reaction mixture was added 0.5 N aqueous solution of sodium hydroxide, followed by extraction with three portions of chloroform and washing with water. The organic layer from the extraction was dried over anhydrous sodium sulfate, and then the solvent was distilled off under reduced pressure to yield 475 mg of the residue of the extract. Said residue was chromatographed on silica gel column. There was obtained 368 mg of 1-[5-(3,4,5-trimethoxyphenyl)-2,4-pentadienoyl,]-piperazine from the eluate fractions with chloroform-methanol (96:4).

To a solution of 266 mg of said piperazine derivative in 10 ml of dry toluene were added in an atmosphere of argon a solution of 146 mg of N-chloroacetylpyrrolidine in 2 ml of dry toluene and subsequently 1.24 ml of triethylamine. The mixture was reacted by heating under reflux for 3.5 hours. After cooled, water was added to the reaction mixture, followed by extraction with three portions of methylene chloride and washing with water. The organic layer from the extraction was dried over anhydrous sodium sulfate. Then the solvent was removed by distillation under reduced pressure to yield 391 mg of the residue of the extract. Said residue was chromatographed on silica gel column. There was obtained 197 mg of 1-[5-(3,4,5-trimethoxyphenyl)-2,4-pentadienoyl]-4-(pyrrolidinocarbonylmethyl)-piperazine. Spectrophotometric data of the product support the structure of the formula (II) shown below.

IR$\gamma_{max}^{CHCl_3}$ (cm$^{-1}$): 1645, 1600, 1585

$^1$H—NMR(deutero chloroform) δ(ppm): 1.80–2.14(4H), 2.47–2.77(4H), 3.17(2H,s), 3.30–3.82 (8H), 3.84(3H,s), 3.87(6H,s), 6.40 (1H,d,J=14 Hz)

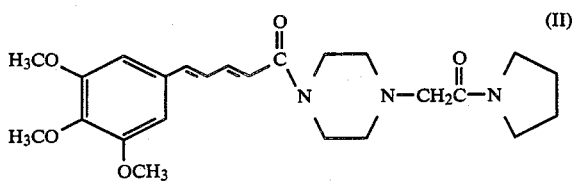

(II)

EXAMPLE 2

To a solution of 320 mg of 1-[5-(3,4,5-trimethoxyphenyl)-2,4-pentadienoyl]-piperazine in 10 ml of dry toluene were added in an atmosphere of argon 131 mg of N-isopropylchloroacetamide and subsequently 0.70 ml of triethylamine. The mixture was heated under reflux for 6.5 hours. After cooled, water was added to the reaction mixture, followed by extraction with three portions of methylene chloride and washing with water. The organic layer from the extraction was dried over anhydrous sodium sulfate, and the solvent was removed by distillation under reduced pressure to give 421 mg of the residue of the extract. Said residue was chromatographed on silica gel column. There was obtained 364 mg of 1-[5-(3,4,5-trimethoxyphenyl)-2,4-pentadienoyl]-4-(N-isopropylaminocarbonylmethyl)-piperazine from eluate fractions with chloroform-methanol (97:3). Spectrophotometric data of the product support the structure of the formula (III) shown below.

IR$\gamma_{max}^{CHCl_3}$ (cm$^{-1}$): 3375, 1665, 1640, 1615, 1600, 1580

$^1$H-NMR(deutero chloroform)δ(ppm): 1.18(6H,d,J=7 Hz), 2.40–2.67(4H), 3.00 (2H,s), 3.50–3.83(4H), 3.83(3H,s), 3.86(6H,s), 6.38(1H,d,J=14 Hz)

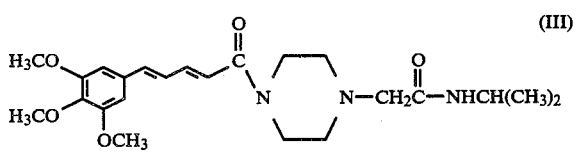

(III)

EXAMPLE 3

To a solution of 279 mg of 1-[5-(3,4,5-trimethoxyphenyl)-2,4-pentadienoyl,]-piperazine in 10 ml of dry toluene were added a solution of 155 mg of N,N-dimethylchloroacetamide in a mixed solvent of 1 ml of dry toluene and 1 ml of dry chloroform and subsequently 0.82 ml of triethylamine in an atmosphere of argon. The mixture was heated under reflux for 4.5 hours. After cooled, water was added to the reaction mixture, followed by extraction with three portions of methylene chloride and washing with water. The organic layer from the extraction was dried over anhydrous sodium sulfate, and the solvent was removed by distillation under reduced pressure to give 429 mg of the residue of the extract. Said residue was chromatographed on silica gel column. There was obtained 313 mg of 1-[5-(3,4,5-trimethoxyphenyl)-2,4-pentadienoyl]-4-(N,N-dimethylaminocarbonylmethyl)-piperazine from the eluate fractions of chloroform-methanol (97:3). Spectrophotometric data of the product support the structure of the formula (IV) shown below.

IR$\gamma_{max}^{CHCl_3}$ (cm$^{-1}$) : 1640, 1615, 1600, 1585

$^1$H-NMR(deutero chloroform) δ(ppm): 2.42 2.70(4H), 2.93(3H,s), 3.05(3H,s), 3.37 (2H,s), 3.57–3.80(4H), 3.83(3H,s), 3.86(6H,s), 6.40(1H,d,J=14 Hz)

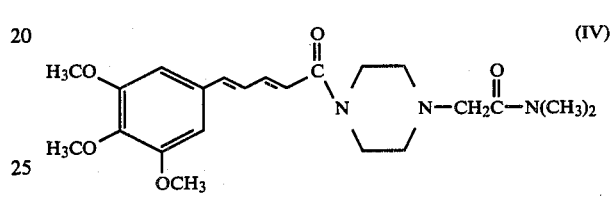

(IV)

EXAMPLE 4

To a solution of 302 mg of 1-[5-(3,4,5-trimethoxyphenyl)-2,4-pentadienoyl]-piperazine in dry toluene (12 ml) were added in an atmosphere of argon 1.3 ml of triethylamine and subsequently a solution of 254 mg of N-methylchloroacetamide in dry toluene-chloroform (1:1, 2 ml). The mixture was refluxed for 8 hours. To the reaction mixture was added water, and extraction was made with methylene chloride. The organic layer was concentrated under reduced pressure, and the residue thus obtained was chromatographed on silica gel column. There was obtained 263 mg of 1-[5-(3,4,5-trimethoxyphenyl)-2,4-pentadienoyl]-4-(methylaminocarbonylmethyl)-piperazine. Spectrophotometric data of the product support the structure of the formula (V) shown below.

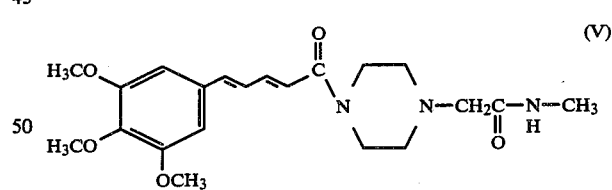

(V)

IR$\gamma_{max}^{CHCl_3}$ (cm$^{-1}$): 3400, 1670, 1640, 1615, 1600, 1580 $^1$H-NMR(deutero chloroform)δ(ppm): 2.3–2.70(4H), 3.68–3.87(each s, total 3H), 3.00(2H,s), 3.37–3.80(4H), 3.82(s,3H), 3.84(s,6H), 6.40(1H,d,J=14 Hz)

TEST EXAMPLE (Vasodilating Activity)

Blood flow in the femoral artery was measured in hybrid adult dogs (weighing about 10 Kg) anesthesized with pentobarbital (30 mg/kg, i.v.) which were subjected to autoperfusion at the left femoral artery under artificial respiration while being equipped with a blood observation probe. The test compound dissolved in 5% ethanol solution was administered through the femoral artery. Percent increase in femoral arterial blood flow after administration of the test compound is shown in Table 1 below in comparison with that prior to the administration.

TABLE 1

| Test compound | Vasodilating Activities | | |
|---|---|---|---|
| | Dose (mg/Kg, Intra-arterial injection) | Number of animals | Increase in femoral arterial blood flow (Δ% ± S.E.) |
| Example 1 | 0.3 | 4 | 50.8 ± 21.3 |
| (Compound of formula II) | 1.0 | 4 | 164.5 ± 47.3 |
| Example 2 | 0.3 | 4 | 42.3 ± 3.8 |
| (Compound of formula III) | 1.0 | 4 | 107.3 ± 14.5 |
| Example 3 | 0.3 | 4 | 32.0 ± 9.0 |
| (Compound of formula IV) | 1.0 | 4 | 75.3 ± 6.2 |
| Example 4 | 0.3 | 4 | 16.8 ± 4.0 |
| (Compound of formula V) | 1.0 | 4 | 66.8 ± 13.7 |
| Cinepazide | 0.3 | 4 | 16.9 ± 6.4 |
| (Control drug) | 1.0 | 4 | 35.9 ± 7.3 |

(Acute Toxicity)

An acute toxicity test was made using ICR male rats (5 weeks old) by oral administration. The $LD_{50}$ values for all of the compounds of the present invention tested were 400 mg/Kg or higher, thereby demonstrating high safety.

What is claimed is:

1. A piperazine compound represented by the formula

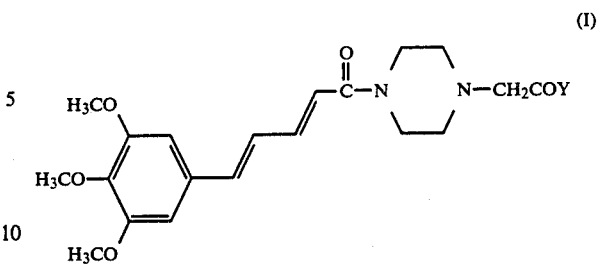

wherein Y represents pyrrolidyl group or a lower alkylamino group.

2. A piperazine compound according to claim 1 wherein Y is pyrrolidyl group.

3. A piperazine compound according to claim 1 wherein Y is methylamino, isopropylamino or dimethylamino.

4. A vasodilator containing a medically effective amount of a piperazine compound having the formula (I) according to claim 1.

5. A vasodilating method for vascular disorders which comprises administering mammals an effective dose of a piperazine compound having the formula (I) according to claim 1.

6. A vasodilating method according to claim 5 wherein the vascular disorder is cerebral, coronary or peripheral vascular disorder.

7. A pharmaceutical composition for the treatment of vascular disorders comprising a vasodilating amount of a piperazine compound having the formula (I) according to claim 1 together with a pharmaceutically acceptable carrier or diluent.

* * * * *

UNITED STATES PATENT AND TRADEMARK OFFICE
CERTIFICATE OF CORRECTION

PATENT NO. : 4,656,172

DATED : April 7, 1987

INVENTOR(S) : Toshio WAKABAYASHI et al

It is certified that error appears in the above-identified patent and that said Letters Patent is hereby corrected as shown below:

Col. 2, line 62, change "trimethoxyphenyl)-2,4-pentadienoyl,]-piperazine" to --trimethoxyphenyl)-2,4-pentadienoyl]-piperazine--.

Col. 3, line 14, delete "$^1$ H" and kindly insert --$^1$H--.

Col. 3, line 16, change "3,84(3H,s)," to --3.84(3H,s),--.

Col. 3, line 62, change "phenyl)-2,4-pentadienoyl,]-piperazine" to --phenyl)-2,4-pentadienoyl]-piperazine--.

Col. 4, line 14, change "2.42" to --2.42- --.

Signed and Sealed this

Sixth Day of October, 1987

Attest:

DONALD J. QUIGG

*Attesting Officer*　　　*Commissioner of Patents and Trademarks*